United States Patent [19]
Benezra

[11] Patent Number: 5,834,298
[45] Date of Patent: Nov. 10, 1998

[54] GENE ENCODING THE HUMAN HOMOLOG OF MAD2

[75] Inventor: Robert Benezra, New York, N.Y.

[73] Assignee: Sloan-Kettering Institute for Cancer Research, New York, N.Y.

[21] Appl. No.: 684,024

[22] Filed: Jul. 19, 1996

Related U.S. Application Data

[60] Provisional application No. 60/001,736, Aug. 1, 1995.

[51] Int. Cl.$^6$ .............................. C07H 21/00; C12Q 1/21; C12Q 1/19; C12Q 5/10
[52] U.S. Cl. ................................. 435/254.21; 435/252.3; 435/320.1; 435/325; 435/348; 435/419; 536/23.1; 536/23.5
[58] Field of Search ................................... 435/91.1, 91.3, 435/172.1, 172.3, 320.1, 325, 419, 254.2, 254.21, 252.3; 530/350; 536/23.1, 23.5; 935/3, 4, 9, 66, 67, 69, 70, 72

[56] References Cited

PUBLICATIONS

Woods et al. The construction of a recombinant cDNA library of the poly(a) + mRNA population from normal human lymphocytes. Nucleic Acids Res. 8(22): 5157–5168, 1980.

Traver et al. Rapid screen ing of a human library in yeast artificial chromosomes for single–copy sequences. Proc. Natl. Acad. Sci. USA 86: 5898–5902. 1989.
Sigma Catalog, 1992.
Armstrong, S.A. et al. (1993) *J. Biolog. Chem.* 268(16):12221–12229.
Li, R., et al. (1993) *Nature* 366: 82–84.
Brown, M.S. and Goldstein, J.L. (1993) *Nature* 366:14–15.
Jiang, Y. et al. (1993) *Nature* 366:84–86.

*Primary Examiner*—George C. Elliott
*Assistant Examiner*—Thomas G. Larson
*Attorney, Agent, or Firm*—John P. White; Cooper & Dunham LLp

[57] ABSTRACT

This invention provides isolated nucleic acid encoding human MAD2, isolated human MAD2 protein. This invention further provides a method of detecting the presence of MAD2 in a tissue sample, a method of determining whether a tumor is susceptible to treatment with a mitotic spindle inhibitor by detecting the presence of MAD2 in the tumor and a method of suppressing tumor formation in a subject which comprises administering the nucleic acid encoding human MAD2 to the subject in an amount effective to enhance expression of MAD2. This invention also provides a nucleic acid reagent capable of detecting the MAD2 gene or gene product and a method for in situ identification of tumors which may be susceptible to treatment with mitotic spindle inhibitors by detecting the absence of nucleic acid encoding MAD2 in the tumor.

12 Claims, 11 Drawing Sheets

FIG. 1

```
hu-Mad2   Malqlsr EQGITLRGS AEI VAEFF SFG INSIL YQRGI YP SETE TR VQKYG
sc-Mad2   M------ SQSISLKGS TRT VTEFF EYS INSIL YQRGV VPAEDEVT VKKYD hu-Mad2   ITFL VTFDLEL IKY LNN VVEQLKD MLYKCSVQ KLV VVISNIESGEV LERW
sc-Mad2   LTIL KTHDELRK ILL QVHR MLGGKCN QLV LCIVDKDEGEV VERM hu-Mad2   QFDIE ------C DKTAKD SAPR eksqkai QDEIRSV IRQIT AT VTFL PL
sc-Mad2   SENVQ hisgnsN GQDDV VDLNTT ------ QSQIRAL IRQIT SS VTFL PE hu-Mad2   E--EVSCSEDLLI YTD KDLV VPEKWEES GPQF ITNSEVRLRS FTTIHK
sc-Mad2   Itk EGGYTFTVLA YTD ADAK VPLEWADSNSKE IPDGEVQFKT SNDHK hu-Mad2   VNSMVAYKipvnd
sc-Mad2   VGAQVSYKKy----
```

FIG. 2A

```
h-MAD2  atg gcg tgcagc tctcc ggg agcagg aa tca ccctgcgcgggagcgc
y-MAD2  atg tca aatcaa tatca taa agggttc aa ca aggacagttaca----- h-MAD2  cgaaatcgtggcc GAGTT CTTC TCA TT GGCAT CAA CAG CATTTT ATA TC
y-MAD2  -------------- GAATT TTTC GAG TA CAGCAT TAA TTC CATTTT GTA CC h-MAD2  AGC GT GGC ATATA TCCA TT GAA acc tt tactcga gtg cagaa atacg ga
y-MAD2  AAA GA GGC GTATA CCCA GA CAGAA gat tt cgtaacg gt aaaaa gtacg at h-MAD2  ct cac ctt gct tgta actac tgat ct tgagctcataaaatacctaaataa
y-MAD2  ct tacg tt act aaag acaca tgat ga tg---------------------- h-MAD2  AACTGAAAGATT ggt tatac aagtg tcag tt cag aaaa c
y-MAD2  AACTGAAAGATT aca tcgg aaaat tctt c taca agtt c h-MAD2  tggttgtag tt a tctcaaat attgaa agt-----------------
y-MAD2  acaggtggc tt ct tggtgga a aatgc aa caattagtattatgtattgta h-MAD2  ------- GGTGAGGT CC TGGAAAGATGG cag tt tgat at tgagtg
y-MAD2  gacaaggatgag GG AGAGGT GG TGGAAAGATGG tcc tt catgt gc aaca h-MAD2  tgacaagactgca aaag at gacagt g cacccaga gaaaag tctc agaaag
y-MAD2  catttctggcaat agca ac gggcag gatgatgtt gtagatt taa atacaa
```

FIG. 2B

```
h-MAD2  ctatccaggatg      AAATC CGTT CAGT GATCAG ACAGATCAC AG TACG GTG
y-MAD2  cacaatcac---      AAATC AGAG CTT TAATCAG GCAAATCAC CT CAAGC GTT h-MAD2  AC A TTTCTGCC actgt tgga agtttctt gt tca tttgatc tgctga ttta
y-MAD2  AC C TTTCTGCC cgaac taac aaaagaag gt ggg tacacat tcacag tact h-MAD2  tacagacaaaga ttt ggt tg tacct gaaaaa tgg gaa ga gt cgggac cac
y-MAD2  tgcatatacaga cgc gga tgc ctaaa gttccg tta gaa tgggc cgact cca h-MAD2  agtt tat tacc aatt ctga ggaa gtgcgcc ttcgt tcattt actacta ca
y-MAD2  atag taagag atac ctga tggt gaagtag ttcaa ttcaaa acattct ct h-MAD2  atccaca aagta aa tagcatg gt ggccta caaaat tcctgtca atgactg
y-MAD2  accaacgatcat aa agttggt gcgcaggt cagcta taaatatt aa----- h-MAD2  a
y-MAD2  -
```

FIG. 3A

```
TGGAAGCGCGTGCTTTTGTTTGTGTCCCTGGCCATGGCGCTGCAGCTCTCCCGGGAGCAG
                                  M  A  L  Q  L  S  R  E  Q    9

GGAATCACCCTGCGCGGGAGCGCCGAAATCGTGGCCGAGTTCTTCTCATTCGGCATCAAC
 G  I  T  L  R  G  S  A  E  I  V  A  E  F  F  S  F  G  I  N   29

AGCATTTTATATCAGCGTGGCATATATCCATCTGAAACCTTTACTCGAGTGCAGAAATAC
 S  I  L  Y  Q  R  G  I  Y  P  S  E  T  F  T  R  V  Q  K  Y   49

GGACTCACCTTGCTTGTAACTACTGATCTTGAGCTCATAAAATACCTAAATAATGTGGTG
 G  L  T  L  L  V  T  T  D  L  E  L  I  K  Y  L  N  N  V  V   69

GAACAACTGAAAGATTGGTTATACAAGTGTTCAGTTCAGAAACTGGTTGTAGTTATCTCA
 E  Q  L  K  D  W  L  Y  K  C  S  V  Q  K  L  V  V  V  I  S   89

AATATTGAAAGTGGTGAGGTCCTGGAAAGATGGCAGTTTGATATTGAGTGTGACAAGACT
 N  I  E  S  G  E  V  L  E  R  W  Q  F  D  I  E  C  D  K  T  109

GCAAAAGATGACAGTGCACCCAGAGAAAAGTCTCAGAAAGCTATCCAGGATGAAATCCGT
 A  K  D  D  S  A  P  R  E  K  S  Q  K  A  I  Q  D  E  I  R  129

TCAGTGATCAGACAGATCACAGCTACGGTGACATTTCTGCCACTGTTGGAAGTTTCTTGT
 S  V  I  R  Q  I  T  A  T  V  T  F  L  P  L  L  E  V  S  C  149

TCATTTGATCTGCTGATTTATACAGACAAAGATTTGGTTGTACCTGAAAAATGGGAAGAG
 S  F  D  L  L  I  Y  T  D  K  D  L  V  V  P  E  K  W  E  E  169

TCGGGACCACAGTTTATTACCAATTCTGAGGAAGTGCGCCTTCGTTCATTTACTACTACA
 S  G  P  Q  F  I  T  N  S  E  E  V  R  L  R  S  F  T  T  T  189

ATCCACAAAGTAAATAGCATGGTGGCCTACAAAATTCCTGTCAATGACTGAGGATGACAT
 I  H  K  V  N  S  M  V  A  Y  K  I  P  V  N  D  *            205

GAGGAAAATAATGTAATTGTAATTTTGAAATGTGGTTTTCCTGAAATCAGGTCATCTATA
GTTGATATGTTTTATTTCATTGGTTAATTTTTACATGGAGAAAACCAAAATGATACTTAC
TGAACTGTGTGTAATTGTTCCTTTTATTTTTTTGGTACCTATTTGACTTACCATGGAGTT
AACATCATGAATTTATTGCACATTGTTCAAAAGGAACCAGGAGGTTTTTTTGTCAACATT
GTGATGTATATTCCTTTGAAGATAGTAACTGTAGATGGAAAAACTTGTGCTATAAAGCTA
GATGCTTTCCTAAATCAGATGTTTTGGTCAAGTAGTTTGACTCAGTATAGGTAGGGAGAT
ATTTAAGTATAAAATACAACAAAGGAAGTCTAAATATTCAGAATCTTTGTTAAGGTCCTG
AAAGTAACTCATAATCTATAAACAATGAAATATTGCTGTATAGCTCCTTTTGACCTTCAT
TTCATGTATAGTTTTCCCTATTGAATCAGTTTCCAATTATTTGACTTTAATTTATGTAAC
TTGAACCTATGAAGCAATGGATATTTGTACTGTTTAATGTTCTGTGATACAGAACAGATT
AATACTCCCTTTTTATCATTACAGTTAGCTAAAAAATTGCCAGGCAGTCCACAAAACAGA
ATTTGCTTTAAGACCAACCCACAGAGTCAGCTGGAGACTAACGGCGCTGGGCCTGCTGG
GCCGGGATATAGTCGTGTTTAGCTAAGTGTCGAGAGCATTAAGAAGAAAGTCCTGGTTGG
AGGCGCAAGGCCTGCAGCACCAGCTGTGGAATCCCCAATAATGT
```

FIG. 3B

```
hsMAD2    1  M A L Q L S R E Q G I T L R G S A E I V A E F F S F G I N S I L Y   33
XMAD2     1  M A G Q L T R - E G I T L K G S A E I V S E F F C G I N S I L Y   32
scMAD2    1  - - - M S Q S I S L K G S T R T V T E F F E Y S I N S I L Y      27 hsMAD2   34  Q R G I Y P S E T F T R V Q K Y G L T L L V T T D L E L I K Y L N   66
XMAD2    33  Q R G I Y P S E T F T I R Q K Y G L T L L V S T D P A L K E Y L N   65
scMAD2   28  Q R G V Y P A E D F V T K K Y D L T L L K T H D D E L K D Y I R      60 hsMAD2   67  N V E Q L K D W L Y K C S V Q K L V V V I S N I E S G E V L E R   99
XMAD2    66  Q L K D W L Y K C Q V Q K L V V V I T S I D S N E I L E R           98
scMAD2   61  K I L L Q V H R W L L G G K C N Q L V L C I V D K D E G E V V E R    93 hsMAD2  100  W Q F D I E C D K T A K D S A P R E K S Q K A I Q D E I R S V I   132
XMAD2    99  W Q F D I E C D K T V K D G - I V R E K S Q K V I Q E E I R S V I   130
scMAD2   94  W S F N V Q H I S G N S N G - Q D D V V D L N T T Q S Q I R A L I    125 hsMAD2  133  R Q I T A T V T F L P L L E V S - - C S F D L L I Y T D K D L V   163
XMAD2   131  R Q I T A T V T F L P L L E T A - - C A F D L L I Y T D K D L E V   161
scMAD2  126  R Q I T S S V T F L P E L T K E G G Y T F T V L A Y T D A D A K V   158 hsMAD2  164  P E K W E E S G P Q F I T N S E E V R L R S F T T T I H K V N S M   196
XMAD2   162  P E K W E E S G P Q F V S N S E E V R L R S F T T T I H K V N S M   194
scMAD2  159  P L E W A D S N S K E I P D G E V V Q F K T F S T N D H K V G A Q   191 hsMAD2  197  V A Y K I P V N D                                                  205
XMAD2   195  V A Y K K I D T F                                                 203
scMAD2  192  V S Y K Y - - - -                                                 196
```

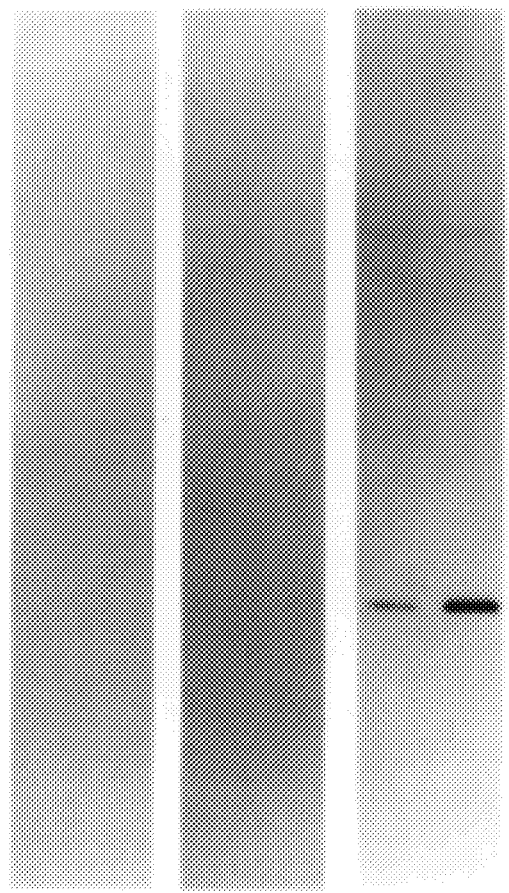

FIG. 4A-1 Buffer
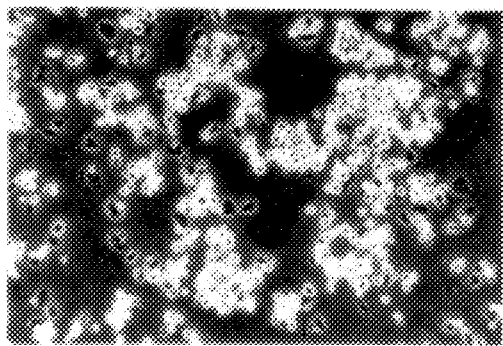
FIG. 4A-2 Preimmune
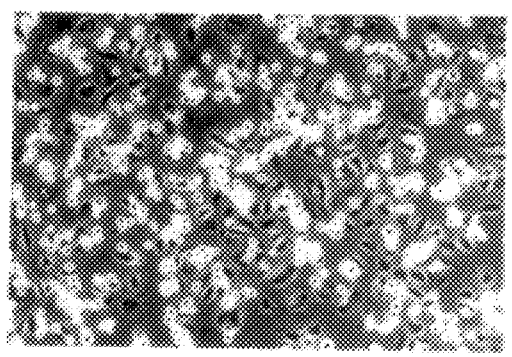
α-hsMad2Δ
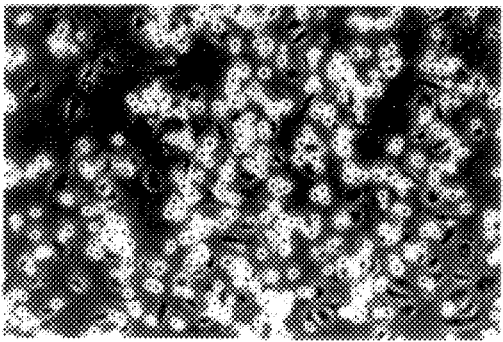
α-hsMad2
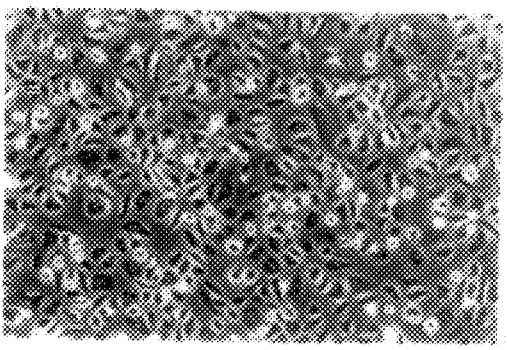
FIG. 4A-3
FIG. 4A-4

FIG. 5A-1
Preimmune
FIG. 5A-2
Anti-hsMAD2Δ
FIG. 5A-3
Anti-hsMAD2
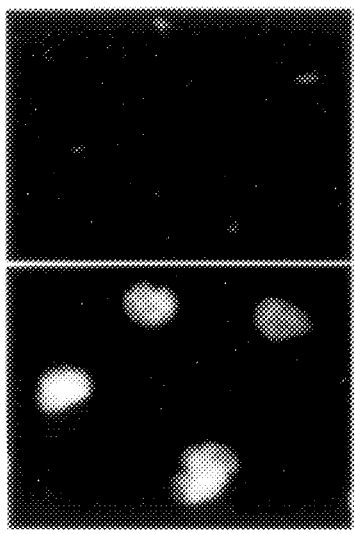
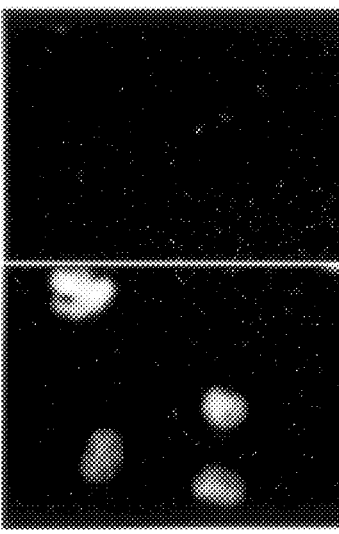
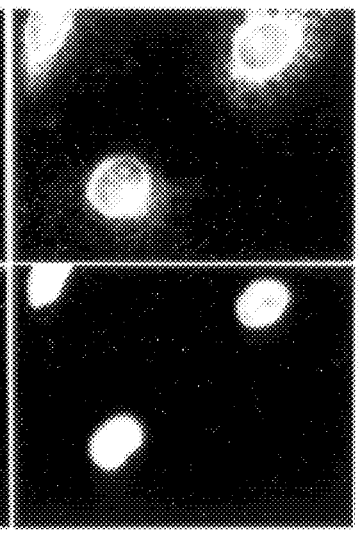
FIG. 5A-4
FIG. 5A-5
FIG. 5A-6

FIG. 5B-2 NOC 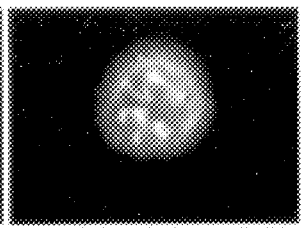

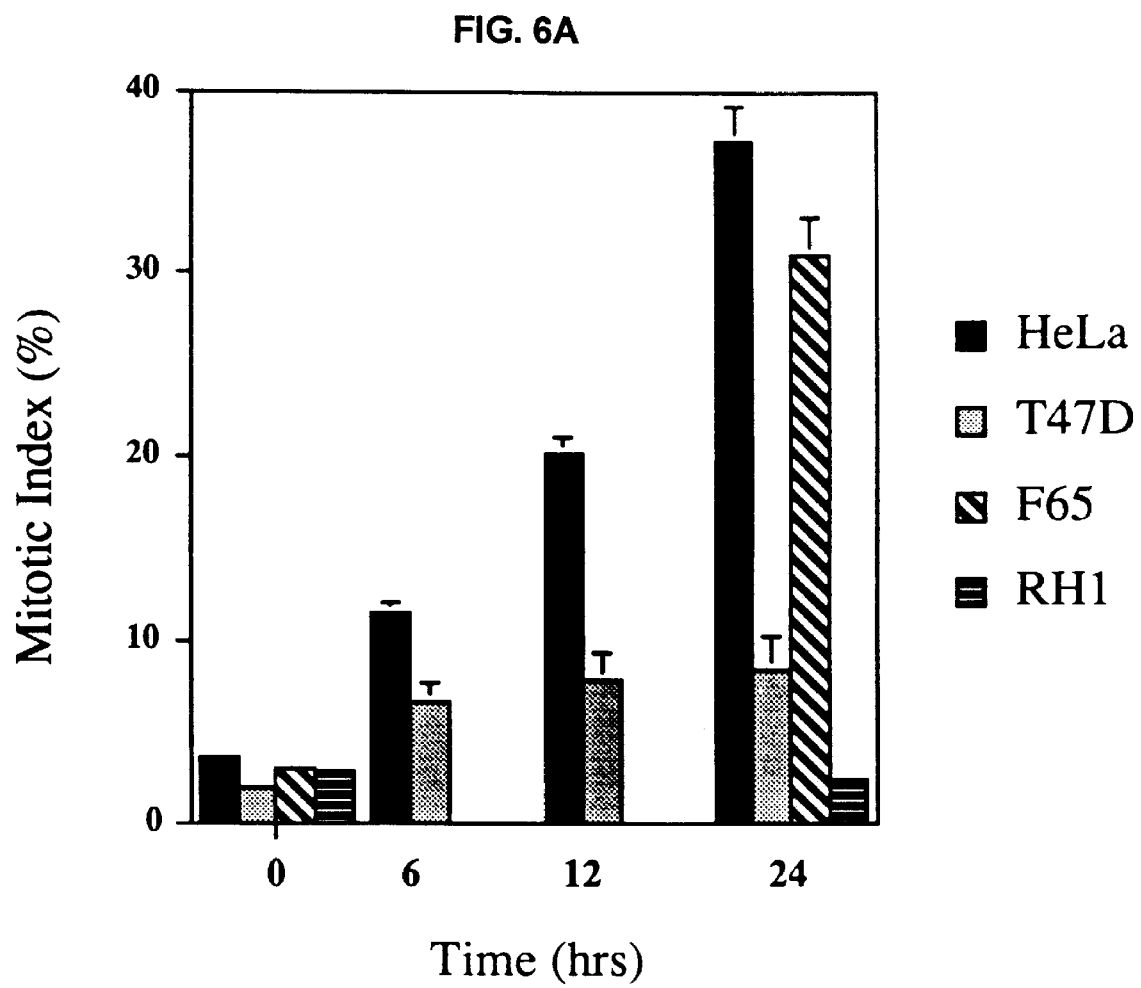

GENE ENCODING THE HUMAN HOMOLOG OF MAD2

The invention disclosed herein was made in the course of work under NCI Core Grant No. 08748 from the National Cancer Institute and NSF Grant No. IBN-9118977 from the National Science Foundation. Accordingly, the U.S. Government has certain rights in this invention.

This application claims the benefit of copending U.S. Provisional application Ser. No. 60/001,736, filed Aug. 1, 1995.

Throughout this application, various publications are referenced by Arabic numerals in brackets. Full citations for these publications may be found at the end of the specification immediately preceding the claims. The disclosures of these publications are in their entirety hereby incorporated by reference into this application to more fully describe the state of the art to which this invention pertains.

BACKGROUND OF THE INVENTION

MAD2 is a mitotic checkpoint gene whose function is required for yeast cells to arrest before undergoing cell division if the mitotic spindle apparatus is improperly attached to the chromosomes. (Li and Murray). In the absence of functional MAD2 protein, yeast cells which are exposed to drugs which inhibit the formation of a mitotic spindle, such as benomyl, vinblastine, nocodozole, etc. undergo rapid cell death due to massive chromosome loss. Yeast cells which have a functional MAD2 protein can survive such drug treatment because they are able to stop dividing prior to the chromosome loss event.

The interest in the MAD2 gene stems from the possibility that tumor cells that are hypersensitive to chemotherapeutic agents which inhibit the formation of the mitotic spindle may be sensitive to these drugs precisely because they are defective in the MAD2 checkpoint. Analysis of the MAD2 status of a given tumor may therefore be a predictor of chemosensitivity. In addition, the loss of MAD2 function in a normal cell may predispose that cell to aberrant chromosome segregation events, a hallmark of tumor progression.

SUMMARY OF THE INVENTION

This invention provides isolated nucleic acid encoding human MAD2 protein.

This invention also provides a vector comprising the nucleic acid encoding human MAD2 protein and a host cell containing the vector.

This invention also provides a nucleic acid probe comprising a nucleic acid molecule comprising at least 15 nucleotides capable of specifically hybridizing with a unique nucleotide sequence included within the nucleotide sequence of the isolated nucleic acid encoding human MAD2 protein.

This invention further provides an antisense oligonucleotide having a sequence capable of specifically hybridizing to mRNA encoding human MAD2 protein so as to prevent translation of the mRNA. This invention further provides a vector comprising the antisense oligonucleotide and a host cell containing the vector.

This invention also provides isolated human MAD2 protein.

This invention also provides an antibody capable of specifically binding to the isolated human MAD2 protein.

This invention further provides a method of detecting the presence of human MAD2 protein in a sample which comprises:

a) contacting the sample with the antibody capable of specifically binding to the isolated human MAD2 protein, under conditions permitting the formation of a complex between the antibody and the human MAD2 protein in the sample; and b) detecting the complex formed in step (a), thereby detecting the presence of human MAD2 protein in the sample.

This invention further provides a method of detecting the expression of MAD2 in a sample which comprises:

a) contacting the sample with the nucleic acid probe comprising a nucleic acid molecule comprising at least 15 nucleotides capable of specifically hybridizing with a unique nucleotide sequence included within the nucleotide sequence of the isolated nucleic acid encoding human MAD2 protein, under conditions permitting the hybridization of the probe to any of the RNA present in the sample; and b) detecting the presence of the hybridized probe, a positive detection indicating the expression of MAD2 in the sample.

This invention further provides a method of determining the susceptibility of a tumor sample to treatment with a mitotic spindle inhibitor by detecting the presence of human MAD2 protein in the tumor which comprises steps of:

a) contacting the tumor sample with the antibody capable of specifically binding to human MAD2 protein, under conditions permitting formation of a complex between the antibody and the human MAD2 protein in the tumor sample; and b) detecting the complex formed in step (a), the presence of the complex indicating that the tumor is susceptible to treatment with a mitotic spindle inhibitor.

This invention also provides a method of determining whether a tumor is susceptible to treatment with a mitotic spindle inhibitor by detecting the presence of MAD2 protein in the tumor which comprises:

a) contacting a tumor sample with the nucleic acid probe comprising a nucleic acid molecule comprising at least 15 nucleotides capable of specifically hybridizing with a unique nucleotide sequence included within the nucleotide sequence of the isolated nucleic acid encoding human MAD2 protein, under conditions permitting the hybridization of the probe to the RNA present in the sample; and b) detecting the presence of the hybridized probe, a positive detection indicating susceptibility to treatment with a mitotic spindle inhibitor.

This invention also provides a pharmaceutical composition comprising an amount of the nucleic acid encoding human MAD2 protein capable of passing through a cell membrane effective to enhance the expression of MAD2 and a suitable pharmaceutically acceptable carrier.

This invention further provides a method of suppressing tumor formation in a subject which comprises administering the nucleic acid encoding human MAD2 protein to the subject in an amount effective to enhance expression of MAD2. This invention also provides a method of suppressing tumor formation in a subject which comprises administering the pharmaceutical composition to the subject.

This invention also provides a pharmaceutical composition comprising an amount of the antisense oligonucleotide having a sequence capable of specifically hybridizing to mRNA encoding for human MAD2 protein so as to prevent translation of the mRNA, which is capable of passing through a cell membrane and effective to inhibit the expression of MAD2 and a suitable pharmaceutically acceptable carrier.

This invention also provides a nucleic acid reagent capable of detecting the MAD2 gene or gene product.

This invention also provides a method for in situ identification of tumors which may be susceptible to treatment with mitotic spindle inhibitors by detecting the absence of nucleic acid encoding MAD2 in the tumor which method comprises contacting the tumor with a suitably labeled nucleic acid reagent capable of detecting the MAD2 gene or gene product.

Other uses and objectives of this invention will apparent to those of ordinary skill in the art in view of the Detailed Description which follows. Such other uses and objectives are deemed to be within the scope of the claims which follow.

BRIEF DESCRIPTION OF THE FIGURES

FIGS. 2A and 2B Side by side comparison of the yeast MAD2 SEQ ID NO. 4 and human MAD2 SEQ ID NO. 3 nucleic acid sequences.

Figures 1, 5B:
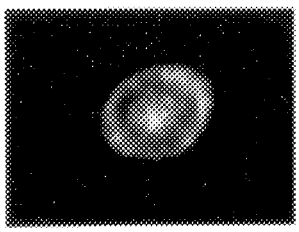
FIG. 1 Side by side comparison of the yeast MAD2 SEQ ID NO. 2 and human MAD2 SEQ ID NO. 1 amino acid sequences.
Figures 3, 5B:
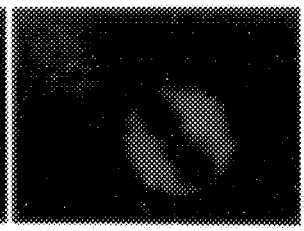
FIGS. 3A–C Characterization of human MAD2.
Figures 4, 5B:
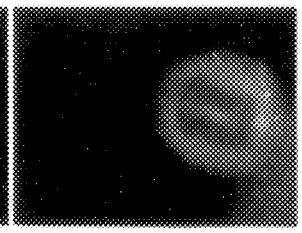
Figures 5, 5B:
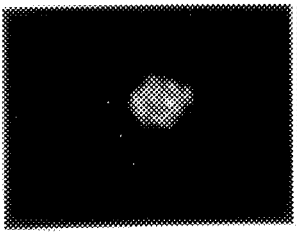

A) Nucleotide SEQ ID NO. 5 and the predicted amino acid SEQ ID NO. 6 acid sequences of hsMAD2 cDNA. The amino acid sequence predicted by the hsMAD2 open reading frame is indicated in single-letter code. The stop codon is indicated with the asterisk.

B) Alignment of the predicted hsMad2 protein sequence SEQ ID NO. 7 with those of X. laevis Mad2 SEQ ID NO. 8 and S. cerevisiae Mad2p SEQ ID. NO. 9. Amino acids identical in at least two of the three MAD2 proteins are boxed. Dashes indicate gaps.

C) Human MAD2 encodes a 24 kD protein. Total protein extracts from HeLa cells (lanes 1, 3, and 5) or HeLa cells transiently transfected with pCMV5-hsMAD2 for 48 hr (lanes 2, 4, and 6) were resolved by 12% SDS-PAGE (30 μg of protein per lane), transferred to nitrocellulose, and probed with the preimmune IgG (lanes 1 and 2), the α-hsMad2Δ IgG (lanes 3 and 4) or the affinity-purified α-hsMad2 antibody (lanes 5 and 6). The positions of prestained kleidoscope molecular mass markers (in kilodaltons, Bio-Rad) are shown on the right.

FIGS. 4A1–4 Human MAD2 functions as a mitotic checkpoint gene.

HeLa cells electroporated with α-hsMad2 antibodies fail to arrest in mitosis in the presence of nocodazole. HeLa cells were electroporated with buffer, the preimmune IgG the α-hsMad2Δ IgG, or the affinity-purified α-hsMad2 antibody as indicated. Electroporated cells were allowed to attach to the plates for 6 hours and then treated with 200 nM nocodazole for additional 18 hours before being photographed.

FIG. 5A(1–6)-B(1–12) Subcellular localization of hsMad2 in HeLa cells.

A1–6) Subcellular localization of hsMad2 during interphase. HeLa cells were stained with the preimmune IgG, the α-hsMad2Δ IgG, or the affinity-purified α-hsMad2 antibody as indicated (top row). DNA was visualized with DAPI (bottom row). Cells were observed with a 40x oil immersion objective.

B1–12) Subcellular localization of hsMad2 during mitosis. HeLa cells were triple stained with affinity-purified α-hsMad2 antibody (top row), human α-centromere serum (middle row), and DAPI (bottom row). Cells in prometaphase (PM), arrested in prometaphase by nocodazole treatment (NOC), metaphase (M), and anaphase (A) are shown. Cells were observed with a 100x oil immersion objective.

Figures 5, 5B, 6:
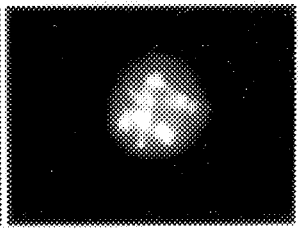
Figures 5, 5B, 6, 7:
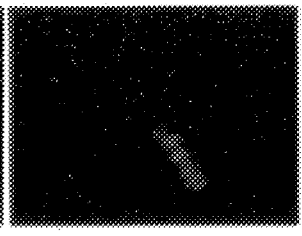
Figures 5, 5B, 6, 7, 8:
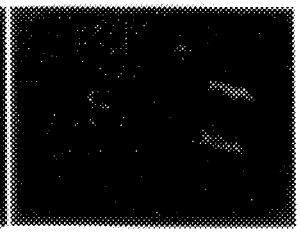
Figures 5, 5B, 6, 7, 8, 9:
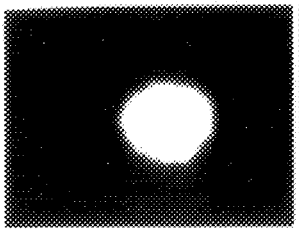
Figures 5, 5B, 6, 7, 8, 9, 10:
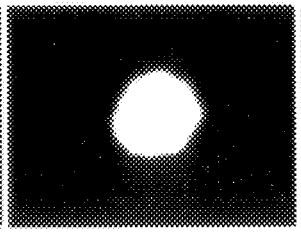
Figures 5, 5B, 6, 7, 8, 9, 10, 11:
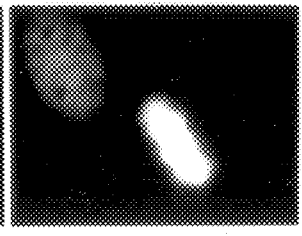
Figures 5, 5B, 6, 7, 8, 9, 10, 11, 12:
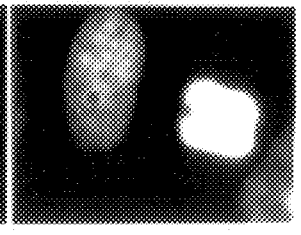
Figure 6B:
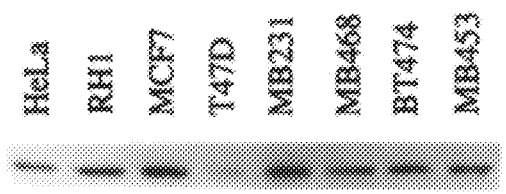

FIGS. 6A–B T47D cells fail to arrest in mitosis in response to nocodazole treatment and are defective for hsMAD2 expression.

A) T47D and RH1 fail to undergo mitotic arrest upon nocodazole treatment. Exponentially growing HeLa, F65, T47D, and RH1 cells were treated with 100 nM nocodazole and harvested at the indicated time points. Cells were transferred to slides by cytospinning, stained with DAPI, and then scored for their mitotic indeces (M.I.). For each cell line, three independent experiments were performed and the average M.I. is shown.

B) T47D is defective for hsMAD2 expression. Equal amounts of total protein extracts from the indicated cell lines were resolved by 12% SDS-PAGE, transferred to nitrocellulose, and probed with α-hsMad2 serum (1:500 dilution).

DETAILED DESCRIPTION OF THE INVENTION

This invention provides isolated nucleic acid encoding human MAD2 protein. The nucleic acid of this invention can be DNA or RNA. In separately preferred embodiments when the nucleic acid is DNA it may be genomic DNA or cDNA. In another preferred embodiment when the nucleic acid is DNA it has a nucleic acid sequence substantially similar to the nucleic acid sequence of FIG. 3A SEQ ID NO. 5. In a further embodiment, the DNA sequence is as set forth in FIG. 3A SEQ ID NO. 5. In another preferred embodiment when the nucleic acid is RNA it may be mRNA.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

In one embodiment of the invention the cDNA is labeled with a detectable moiety. Substances which function as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin.

In a preferred embodiment the nucleic acid of the subject invention encodes a protein having an amino acid sequence substantially similar to the amino acid sequence of FIG. 3A SEQ ID NO. 6.

This invention also provides a replicable vector comprising the nucleic acid encoding human MAD2 protein and a host cell containing the vector. In one embodiment the host cell is a prokaryotic or eukaryotic cell. In an embodiment wherein the the host cell is a prokaryotic, it is a bacterial cell. In still another embodiment wherein the host cell is a eukaryotic cell, the host cell may be a yeast, insect, plant, or a mammalian cell.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk cells and COS cells. Mammalian cells may be transfected by methods well known in the art such as calcium phosphate precipitation, electroporation and microinjection.

This invention further provides a method of producing a polypeptide having the biological activity of the MAD2 protein which comprising growing host cells of a vector system containing the MAD2 protein sequence under suitable conditions permitting production of the polypeptide and recovering the polypeptide so produced.

This invention also provides a nucleic acid probe comprising a nucleic acid molecule comprising at least 15 nucleotides capable of specifically hybridizing with a unique nucleotide sequence included within the nucleotide sequence of the isolated nucleic acid encoding human MAD2 protein.

In a preferred embodiment the nucleic acid probe comprises DNA. In an additionally preferred embodiment the nucleic acid probe comprises RNA.

This invention further provides an antisense oligonucleotide having a sequence capable of specifically hybridizing to mRNA encoding human MAD2 protein so as to prevent translation of the mRNA. This invention further provides a replicable vector comprising the antisense oligonucleotide and a host cell containing the vector.

In one embodiment the antisense oligonucleotide has a sequence capable of specifically hybridizing to mRNA so as to prevent translation of the mRNA. In the practice of this invention the antisense oligonucleotide may be contained within a replicable vector. In the practice of this invention the vector may be contained within a host cell. In one embodiment the host cell is a prokaryotic or eukaryotic cell. In an embodiment wherein the host cell is a prokaryotic, it is a bacterial cell. In still another embodiment wherein the host cell is a eukaryotic cell, the host cell may be a yeast, insect, plant, or a mammalian cell.

This invention also provides isolated human MAD2 protein. In the preferred embodiment the isolated human MAD2 protein has an amino acid sequence substantially similar to the amino acid sequence shown in FIG. 3A SEQ ID NO. 6.

This invention also provides an antibody capable of specifically binding to the isolated human MAD2 protein. In a preferred embodiment the antibody is capable of specifically binding to the protein having the amino acid sequence shown in FIG. 3A SEQ ID NO. 6.

In one embodiment the antibody is a monoclonal antibody. In a separate embodiment the antibody is a polyclonal antibody.

Polyclonal antibodies may be produced by injecting a host animal such as rabbit, rat, goat, mouse or other animal with the immunogen of this invention. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention the antibodies can be labeled with a detectable moiety. As noted above, a "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin.

This invention further provides a method of detecting the presence of human MAD2 protein in a sample which comprises:
   a) contacting the sample with the antibody, wherein the antibody is labeled with a detectable moiety and is capable of specifically binding to a human MAD2 protein, under conditions permitting the formation of a complex between the antibody and the human MAD2 protein in the sample; and
   b) detecting the complex formed in step (a), thereby detecting the presence of human MAD2 protein in the sample.

In a preferred embodiment the detection in step (b) is performed by detection of a detectable moiety on the antibody which may be a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin.

As used herein, "sample" means body tissue or fluid, including but not limited to blood, urine, saliva, and cerebrospinal fluid.

This invention further provides a method of detecting the expression of MAD2 in a sample which comprises:
   a) contacting the sample with a nucleic acid probe, wherein the probe is labeled with a detectable moiety and comprises at least 15 nucleotides capable of specifically hybridizing with a unique nucleotide sequence included within the nucleotide sequence of the isolated nucleic acid encoding human MAD2 protein, under conditions permitting the hybridization of the probe to the RNA present in the sample; and
   b) detecting the presence of the hybridized probe, a positive detection indicating the expression of MAD2 in a sample.

The term "probe" as used herein refers to any nucleic acid molecule which can be labeled and which forms a double helix by binding with a molecule containing a nucleic acid sequence of interest through complementary base paring. Those skilled in the art also refer to such probes as "hybridization probes." For example, when using a DNA probe to locate a DNA sequence of interest, a sample containing double stranded DNA can be reacted with the DNA probe to locate any DNA molecule in a sample which comprises the sequence of interest ("target DNA"). In such methods, the double stranded DNA in the sample is disassociated into its single strands and then reacted with a DNA probe. The probe binds to any target DNA in the sample by complementary base paring, i.e., adenine matches with thymidine and guanine with cytosine. The DNA probe, therefore, is a single strand of a DNA double helix which comprises nucleic acid molecules which are complementary to the sequence of interest.

Methods of making labeled nucleic acid probes, both DNA and RNA, are well known to those of ordinary skill in the art.

As used herein, the phrase "specifically hybridizing" means the ability of a nucleic acid molecule to recognize a nucleic acid sequence sufficiently similar to its own so as to form double-helical segments through hydrogen bonding between complementary base pairs. As used herein, a "unique sequence" is a sequence specific to only the nucleic acid molecules encoding the human MAD2 protein.

In a preferred embodiment the detection in step (b) is performed by detection of a detectable moiety on the probe which may be a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin.

This invention further provides a method of determining the susceptibility of a tumor sample to treatment with a mitotic spindle inhibitor which comprises steps of:
   a) contacting the tumor sample with an antibody, wherein the antibody is labeled with a detectable moiety and is capable of specifically binding to a human MAD2 protein, under conditions permitting the formation of a complex between the antibody and the human MAD2 protein in the tumor sample; and
   b) detecting the complex formed in step (a), the presence of the complex indicating that the tumor is susceptible to treatment with a mitotic spindle inhibitor.

In a preferred embodiment the detection in step (b) is performed by detection of a detectable moiety on the antibody which may be a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin.

This invention also provides a method of determining whether a tumor is susceptible to treatment with a mitotic spindle inhibitor by detecting the presence of MAD2 protein in the tumor which comprises:
   a) contacting a tumor sample with a nucleic acid probe, wherein the probe is labeled with a detectable moiety and comprises at least 15 nucleotides capable of specifically hybridizing with a unique sequence included within the sequence of the isolated nucleic acid encoding for human MAD2, under conditions permitting the hybridization of the probe to the RNA present in the sample; and b) detecting the presence of the hybridized probe, a positive detection indicating susceptibility to treatment with a mitotic spindle inhibitor.

In a preferred embodiment the detection in step (b) is performed by detection of a detectable moiety on the probe which may be a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin.

This invention also provides a pharmaceutical composition comprising an amount of the nucleic acid encoding human MAD2 protein capable of passing through a cell membrane effective to enhance the expression of MAD2 and a suitable pharmaceutically acceptable carrier.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules.

Typically such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In addition to the standard characteristics of the pharmaceutically acceptable carriers, the "suitable" carriers of the subject are further characterized as being able to penetrate the cell membrane. Therefore in one embodiment of the pharmaceutical composition the pharmaceutically acceptable carrier binds to a receptor on a cell capable of being taken up by the cell after binding to the structure.

In a preferred embodiment of the pharmaceutical composition the pharmaceutically acceptable carrier is capable of binding to a receptor which is specific for a selected tumor cell type.

This invention further provides a method of suppressing tumor formation in a subject which comprises administering the nucleic acid encoding human MAD2 protein to the subject in an amount effective to enhance expression of MAD2. This invention also provides a method of suppressing tumor formation in a subject which comprises administering the pharmaceutical composition to the subject.

In the practice of this invention, the administration of the nucleic acid or pharmaceutical composition comprising the nucleic acid may be effected by any of the well known methods including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments or transdermal patches.

This invention also provides a pharmaceutical composition comprising an amount of the antisense oligonucleotide having a sequence capable of specifically hybridizing to mRNA encoding for human MAD2 protein so as to prevent translation of the mRNA, which is capable of passing through a cell membrane and effective to inhibit the expression of MAD2 and a suitable pharmaceutically acceptable carrier.

In a preferred embodiment the pharmaceutical composition comprises an amount of the antisense oligonucleotide capable of passing through a cell membrane and effective to inhibit the expression of MAD2 and a suitable pharmaceutically acceptable carrier.

In a particularly preferred embodiment the pharmaceutical composition the oligonucleotide is coupled to a substance which inactivates mRNA. Examples of such "substances" include, but are not limited to, ribozymes. In this embodiment the pharmaceutically acceptable carrier may be capable of binding to a receptor on a cell capable of being taken up by the cell after binding to the structure. In this embodiment of the pharmaceutical composition the pharmaceutically acceptable carrier may additionally be capable of binding to a receptor which is specific for a selected tumor cell type.

Finally, this invention also provides a nucleic acid reagent capable of detecting the MAD2 gene or gene product. The nucleic acid reagent can be used in a method for in situ identification of tumors which may be susceptible to treatment with mitotic spindle inhibitors by detecting the absence of nucleic acid encoding MAD2 in the tumor. Such method comprises contacting the tumor with a suitably labeled nucleic acid reagent capable of detecting the MAD2 gene or gene product.

In the practice of this aspect of the invention the suitably labeled nucleic acid reagent comprises a detectable moiety chosen from the group consisting of a fluorescent label, a radioactive atom, a paramagnetic ion, biotin, a chemiluminescent label and a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin.

This invention provides a recombinant non-human vertebrate animal wherein functional hsMAD2 protein is not expressed. As used herein, recombinant animals are the animals or their ancestors, which have been manipulated by recombinant technology. In an embodiment, the animal is a rodent. In a preferred embodiment, the rodent is a mouse. These recombinant animals will be useful for study of tumorigenesis. Methods to make these animals are known in the art. Sometimes these animals may be called "knock-out" animal as the gene coding for hsMAD2 is rendered non-functional.

The following Experimental Details are provided to aid in the understanding of the invention. The Experimental Details are not intended, and should not be interpreted, to limit the scope of the invention which is more fully defined in the claims which follow.

EXPERIMENTAL DETAILS

First Series of Experiments

Example 1: Isolation of human homologue of MAD2 as a high-copy number suppressor of cbf1Δ.

Budding yeast strain YNN415 requires exogenous methionine for growth and is supersensitive to the microtubule-destabilizing drug thiabendazole due to the cbf1 null allele. As a means of identifying human clones that could substitute for cbf1, YNN415 was first transformed with a human cDNA library which carries the LEU2 marker by LiCl method (Guthrie and Fink, 1991). About one half million transformants were planted on ten SD-met-leu plates. After 5-day incubation at 30° C., 19 colonies grew up and were subsequently tested for thiabendazole sensitivity on YPD plates containing 100 ug/ml thiabendazole. Among these 19 clones, only one clone grew well on both SD-metleu and YPD+thiabendazole plates. Plasmid DNA from this clone was then recovered by standard methods (Maniatis et al., 1982) and its cDNA insert was sequenced by the dideoxynucleotide method (Maniatis et al., 1982). Analysis of the DNA sequence of the 1.5 kb cDNA insert showed that it contained an open reading frame that encodes a protein of 205 amino acids. We used this 205 amino acid sequence to search the Genbank database and found that only the budding yeast MAD2 showed significant homology to our cDNA clone. The overall protein sequence identity between our clone and yeast MAD2 is about 40% and the overall similarity is about 60%. Therefore, based on the sequence homology, we named our gene human MAD2 (hsMAD2). Retransformation of hsMAD2 into YNN415 showed a weak but reproducible complementation activity of the thiabendazole sensitivity. Although not wishing to be limited to any particular theory, it is believed that hsMAD2 will function similar to yeast MAD2 which has been shown to function as a spindle assembly checkpoint in cell cycle M phase. For example, hsMAD2 may monitor the kinetochore-spindle attachment before anaphase occurs.

Example 2: Generation of anti-MAD2 antibody and chromosomal mapping of hsMAD2.

Full-length hsMAD2 coding sequence was subcloned into the pET28(a) so that a histidine tag was fused in-frame to the N terminus of hsMAD2 protein. Full-length his-hsMAD2 was then overexpressed and purified following manufacturer's instructions. Purified his-hsMAD2 protein was then injected into New Zealand White rabbit to generate anti-hsMAD2 serum. We showed the specificity of our anti-hsMAD2 serum by immunoprecipitating the in vitro translated MAD2 protein and demonstrating that the antibody binding is completed efficiently by the purified protein. Briefly, 1 microgram of MAD2 mRNA was incubated with rabbit reticulocyte lysates (Promega) in the presence of 1 mM amino acids minus methionine and 10 microcuries 35-S-methionine for 1.5 hours at 30° C. in a 50 microliter volume. Five microliters of the reaction was then diluted into 150 microliters of RL-150 buffer (Benezra et al., 1990) and various dilutions of the antisera added (with and without competing polypeptides) before percipitating the complexes with protein A agarose beads (Repligen). The immunoprecipitates were then analyzed by standard SDS-PAGE (Maniatis et al., 1982). By Western blotting (performed as described in Harlow and Lane, 1988) we have shown that anti-hsMAD2 serum specifically recognizes a polypeptide that migrates on SDS-polyacrylamide gels with the expected molecular weight. Transient transfection (performed by the DEAE-dextran method as described in Maniatis et al., 1982) and peptide competition assays showed that the above-mentioned polypeptide corresponds to the endogenous hsMAD2 protein. Immunostaining of Hela cells fixed in 4% paraformaldehyde and permebilized in 0.35% Triton-X-100 was performed by standard methods (Harlow and Lane, 1988) and showed that our anti-hsMAD2 serum can specifically stain certain regions in nuclei that may correspond to the centromeres of chromosomes. This very unusual staining pattern can now be used as a marker for proper MAD2 deposition. Alterations in this pattern, in addition to changes in MAD2 protein levels by Western analysis, can be used to monitor aberrant MAD2 function.

Example 3: Tumor suppression.

To determine whether hsMAD2 functions as a tumor suppressor gene we determined the chromosomal locus of hsMAD2. A P1 human genomic clone that contains hsMAD2 was isolated and used to hybridize to human chromosomes by FISH (fluorescent in situ hybridization). Preliminary data indicates that hsMAD2 maps to a region thought to contain a tumor suppressor locus. One breast tumor line examined (T47D) showed very high sensitivity to taxol and had decreased MAD2 mRNA and protein levels.

EXPERIMENTAL DISCUSSION

The human MAD2 gene was found by a genetic selection procedure carried out in yeast designed to identify molecules which could suppress the sensitivity of a particular strain of yeast to mitotic spindle inhibitors. By overexpressing random protein coding sequences from a human glioma cDNA library in this yeast strain, we were able to select for a yeast cDNA and protein. The h-MAD2 gene can partially suppress the benomyl sensitivity of a mutant yeast strain lacking functional yeast MAD2 directly demonstrating that the human clone is functionally related to the yeast clone. Despite the similarity of the yeast SEQ ID NO. 2 and human SEQ ID NO. 1 protein sequences (see FIG. 1) the nucleotide sequences are sufficiently diverged (see FIG. 2) that use of the yeast sequence SEQ ID NO. 4 in analysis would be impossible.

REFERENCES OF THE FIRST SERIES OF EXPERIMENTS

1. Benezra, R. et al. (1990). Cell 61: 49–59.
2. Harlow, E. and Lane, D. (1988). Antibodies: A Laboratory Manual. (Cold Spring Harbor Press, Cold Spring N.Y.).
3. Maniatis, T. et al. (1982). Molecular Cloning: A Laboratory Manual. (Cold Spring Harbor Press, Cold Spring N.Y.).
4. Li, R. and Murray, A. W. (Aug. 1, 1991). Cell 66: pp. 519–531.

Second Series of Experiments

A cDNA clone which encodes the human homologue of the product of Saccharomyces cerevisiae mitotic checkpoint gene MAD2 was isolated. In yeast, this gene product is required for cells to arrest in mitosis if the mitotic spindle assembly is perturbed (1). HeLa cells electroporated with an affinity purified antibody against human MAD2 protein fail to undergo mitotic arrest in the presence of the microtubule depolymerizing drug nocodazole demonstrating directly that hsMAD2 is a necessary component of the mitotic checkpoint in human cells. Immunofluorescence analysis of HeLa cells indicates that during mitosis, the hsMAD2 protein is localized at the kinetochore after chromosome condensation but is no longer observed at the kinetochore when the chromosomes are aligned at the metaphase plate suggesting that hsMad2 might be a sensor of mitotic spindle attachment. Finally, T47D, a breast tumor cell line which is hypersensitive to taxol and nocodazole treatment, is unable to execute the mitotic checkpoint and has reduced hsMAD2 expression. This result suggests that defects in hsMAD2 may play a role in the observed sensitivity of certain tumors to mitotic spindle inhibitors.

During mitosis, the onset of anaphase is demarcated by the separation of sister chromatids and the destruction of cyclin B which are irreversible events that commit a cell to complete the division cycle (2–4). Mitotic checkpoint control mechanisms (5–8) have evolved which test the cell's preparedness to undergo division and block cell cycle progression prior to the irreversible events associated with anaphase when the mitotic spindle apparatus is not appropriately assembled. For example, defects in the structure of the mitotic spindle, unoccupied microtubule binding sites at the kinetochores, and a lack of tension on the kinetochores supplied by opposing forces on bioriented metaphase chromosomes can all activate the mitotic checkpoint and arrest cells in mitosis (1, 9–12). Progress has been made in identifying some of the molecular components that sense failures in mitotic spindle assembly and send the "stop mitosis" signal. In budding yeast, six non-essential genes have been identified that are required for the execution of the mitotic checkpoint: MAD1–3 (1) and BUB1–3 (9). These genes were identified in screens for mutant cells that are hypersensitive to mitotic spindle inhibitors. Studies in higher eukaryotes have clearly indicated the existence of a similar mitotic checkpoint pathway (10–14), but its molecular components have not yet been identified.

A human cDNA clone was isolated (15) in a screen for high copy number suppressors of the thiabendazole (a mitotic spindle inhibitor) sensitivity observed in yeast cells lacking Cbf1p, a component of the budding yeast kinetochore (18–20). Sequence determination of the cDNA revealed an open reading frame of 205 amino acids SEQ ID NO. 6 (FIG. 3A) that was highly homologous to the product of the budding yeast mitotic checkpoint gene MAD2 (Genbank accession number U14132). With the introduction of two very small gaps (1 and 2 residues), the two proteins are 40% identical and 60% similar over the entire open reading frame (FIG. 3B). The human locus is therefore referred to as hsMAD2 SEQ ID NO. 7 (for homo sapiens MAD2). A MAD2 homologue has also been identified and characterized in Xenopus laevis and the protein sequence alignment is shown in FIG. 3B SEQ ID NO. 8. The protein encoded by the hsMAD2 cDNA has a predicted molecular weight of 23.5 kD with two potential amphipathic alpha helices at residues 64–74 and 124–134. The presence and relative positions of the amphipathic alpha helices are conserved between all three species. The fact that both hsMAD2 and yeast MAD2 can partially suppress the thiabendazole sensitivity of cbf1 null yeast cells (data not shown) suggest the possibility that in the absence of CBF1 the mitotic checkpoint is not fully activated.

To further characterize hsMad2, polyclonal antibodies were generated and affinity-purified (21). In addition, the IgG fractions from the preimmune serum and the α-hsMad2 serum that was first passed over the hsMad2 affinity column (referred to as α-hsMad2Δ IgG) were also isolated (21). By Western analysis (23) the affinity-purified α-hsMad2 antibody specifically recognizes a single protein species of approximately 24 kD in total HeLa cell extracts that is not observed with either preimmune IgG or α-hsMad2Δ IgG (FIG. 3C). Extracts from HeLa cells that have been transiently transfected with a hsMAD2 expression vehicle show an increase in intensity of the 24 kD band indicating that this species is almost certainly encoded by the hsMAD2 cDNA (FIG. 3C, compare lane 6 with lane 5). It is also clear from this analysis that the affinity-purified antibody against hsMad2 is highly specific for the protein expressed in human cells.

In order to determine if hsMAD2 functions as a mitotic checkpoint gene, affinity-purified antibodies against hsMad2 were electroporated into HeLa cells and the status of the mitotic checkpoint was determined (24). If hsMAD2 activity is required for the execution of the mitotic checkpoint, then the α-hsMad2 antibody would be expected to inhibit this activity and prevent mitotic arrest in the presence of mitotic spindle inhibiting drugs. As shown in FIG. 4A, a significant percentage of cells electroporated with either buffer alone, the preimmune IgG or the α-hs Mad2Δ IgG are rounded up after the nocodazole treatment indicative of cells arrested in mitosis (also see below). In contrast, cells electroporated with the α-hsMad2 antibody show far fewer rounded cells after nocodazole treatment (note that 80%~90% of the cells that survive the electroporation have taken up IgG as assayed by immunofluorescence, data not shown). In order to confirm that the α-hsMad2 antibody was quantitatively affecting the mitotic index (M.I.) of the cells exposed to nocodazole, the percentage of IgG+cells in mitosis was determined after the nocodazole treatment of the electroporated cells. As shown in Table 1, whereas the average M.I. of the IgG+cells electrophorated with either the preimmune IgG or the α-hsMad2Δ IgG was about 30% (471/1588), the M.I. of IgG+cells electroporated with the α-hsMad2 antibody was 1.8% (18/1016). This latter result is unlikely to be due to an arrest prior to the onset of mitosis since the cells electroporated with the α-hsMad2 antibody continue to cycle for 30 hours at the same rate as the cells electroporated with the preimmune IgG (data not shown). These data therefore directly demonstrate that hsMad2 is required in human cells for the execution of the mitotic checkpoint in response to nocodazole treatment. Since XMad2 has also been shown to be an essential component of the mitotic checkpont in Xenopus laevis, it is concluded that the mitotic checkpoint function of MAD2 is highly conserved during evolution and probably plays a critical role in ensuring accurate chromosome segregation.

TABLE 1

Summary of the antibody electroporation experiments.

| Experiment | Nocodazole (nM) | Time (hr) | Antibody | IgG+ | IgG+ mitotic cells |
| --- | --- | --- | --- | --- | --- |
| 1 | 100 | 12 | Preimmune | 254 | 52 |
|  |  |  | α-hsMad2 | 206 | 3 |
| 2 | 200 | 18 | Preimmune | 270 | 77 |
|  |  |  | α-hsMad2 | 295 | 6 |
| 3 | 200 | 18 | Preimmune | 261 | 83 |
|  |  |  | α-hsMad2Δ | 233 | 74 |
|  |  |  | α-hsMad2 | 217 | 4 |
| 4 | 200 | 18 | Preimmune | 275 | 94 |
|  |  |  | α-hsMad2Δ | 295 | 91 |
|  |  |  | α-hsMad2 | 298 | 5 |

Four independent experiments have been performed. For preimmune IgG and α-hsMad2Δ IgG electroporations, a total of 1588 IgG+ cells were counted among which 471 are mitotic cells, thereby giving an overall mitotic index of 30%. For α-hsMad2 IgG electroporation, 18 cells were found to be in M phase among 1016 IgG+ cells counted, giving a mitotic index of 1.8%.

Studies in budding yeast (25,26), insect and vertebrate cells (10–14) have pointed to a close link between the kinetochore and the mitotic checkpoint pathway. It was therefore of interest to determine the subcellular localization of hsMad2 (27). During interphase, hsMad2 distributes throughout cells with a non-uniform distribution pattern (FIG. 5A). Specifically, perinuclear and patchy cytoplasmic staining are consistently observed. In mitotic cells, the pattern of hsMad2 staining appears to vary with the stage of mitosis. hsMad2 colocalizes with the kinetochore in those cells in which the chromosomes are highly condensed but not yet aligned at the metaphase plate, presumably in either late prophase or prometaphase (FIG. 5B, this stage is referred to as prometaphase). At metaphase and anaphase however, hsMad2 staining is absent from the chromosomes (FIG. 5B). The kinetochore localization of hsMad2 in prometaphase (when few kinetochores are attached to the mitotic spindle) suggests that hsMad2 may function as a sensor of the spindle-kinetochore interaction and can activate the mitotic checkpoint when the interaction is incomplete. Consistent with this possibility, persistent kinetochore localization of hsMad2 in HeLa cells arrested in mitosis by nocodazole treatment which inhibits the spindle-kinetochore interaction has been observed (28) (FIG. 5B). It is possible that hsMad2 may also monitor other events such as the alignment of the chromosomes at the metaphase plate.

Since yeast cells defective in mitotic checkpoint genes are hypersensitive to mitotic spindle inhibitors, it was necessary to determine if the hypersensitivity to such drugs observed in certain human tumor cells could be accounted for by defects in mitotic checkpoint execution. T47D, a breast tumor cell line, and RH1, a rhabdomyosarcoma cell line, were found to be hypersensitive to taxol and nocodazole (data not shown).

This sensitivity could be accounted for by their failure to undergo mitotic arrest in response to nocodazole treatment as shown in FIG. 6A. Addtionally, T47D cells have been shown to be karyotypically unstable (29), consistent with the idea that they are defective in the mitotic checkpoint. Whether these two cell lines have any defects in hsMAD2 protein expression was examined. By Western analysis T47D has about a 3.5 fold reduction in hsMad2 protein level relative to nocodazole and taxol resistant cell lines (FIG. 6B). RH1 cells on the other hand show no such decrease. This data suggests the possibility that an hsMAD2 defect in T47D contributes to the observed failure to undergo mitotic arrest in response to nocodazole treatment and the resultant hypersensitivity to this compond. In RH1 cells, the mitotic checkpoint defect is either in some other component of the pathway or due to a more subtle change in hsMad2 activity.

It has been shown that the MAD proteins in budding yeast are required for accurate chromosome segregation under normal growth conditions (1). It is reasonable therefore that loss of hsMAD2 function might lead to aberrant chromosome segregation in mammalian cells, an event which leads to genomic instability and has been shown to be associated with tumor formation in a number of cell types (30). This hypothesis can now be tested by the generation and analysis of MAD2 null mice.

REFERENCES OF THE SECOND SERIES OF EXPERIMENTS

1. Li, R. & Murray, A. W. *Cell* 66, 519–531 (1991).
2. Earnshaw, W. C. & Pluta, A. F. *Bioessays* 16, 639–643 (1994).
3. King, R. W., Jackson, P. K., and Kirschner, M. W. *Cell* 79, 563–571 (1994).
4. Murray, A. *Cell* 81, 149–152 (1995).
5. Murray, A. W. *Curr. Opin. Genet. Dev.* 5, 5–11 (1995).
6. Gorbsky, G. J. *Trends Cell Biol.* 5, 143–148 (1995).
7. Hartwell, L. H., and Kastan, M. B. *Science* 266, 1821–1828 (1994).
8. Murray, A. W. *Nature* 359, 599–604 (1992).
9. Hoyt, M. A., Totis, L. & Roberts, B. T. *Cell* 66, 507–517 (1991).
10. Rieder, C. L., Schultz, A., Cole, R. & Sluder, G. J. *Cell Biol.* 127, 1301–1310 (1994).
11. Rieder, C. L., Cole, R. W., Khodjakov, A. & Sluder, G. *J. Cell Biol.* 130, 941–948 (1995).
12. Li, X. & Nicklas, R. B. *Nature* 373, 630–632 (1995).
13. Nicklas, R. B., Ward, S. C. & Gorbsky, G. J. *J. Cell Biol.* 130, 929–939 (1995).
14. Campbell, M. S. & Gorbsky, G. J. *J. Cell Biol.* 129, 1195–1204 (1995).
15. YNN415 (18) (the cbf1 null strain) was transformed with a human cDNA library (kindly provided by Dr. John Colicelli) using a lithium acetate method (16). Approximately $4 \times 10^5$ transformants were plated on YPD plates containing 100 µg/ml thiabendazole (Sigma). After a 6-day incubation at 30° C., 19 clones were isolated and retested for thiabendazole resistance. The thiabendazole resistance of one clone was dependent on the plasmid bearing the human cDNA. Plasmid DNA isolated from this clone contains a 1.5 kb cDNA insert. Nucleotide sequence determination was performed by the dideoxy chain termination method (17) with Sequenase (US Biochemicals).
16. Gietz, D., Jean, A. S., Woods, R. A. & Schiestl, R. H. *Nucl. Acids Res.* 20, 1425 (1992).
17. Sanger, F., Nicklen, S., and Coulson, A. R. *Proc. Nati. Acad. Sci.* USA 74, 5463–5467 (1977).
18. Cai, M. & Davis, R. W. *Cell* 61, 437–446 (1990).
19. Mellor, J., et al. *EMBO J.* 9, 4017–4026 (1990).
20. Baker, R. & Masison, D. *Mol. Cell. Biol.* 10, 2458–2467 (1990).
21. Full-length hsMAD2 open reading frame was subcloned into pET-28a(+). 6His-tagged hsMad2 was overexpressed in BL21 and purified on a Ni-NTA column according to the manufacturer's instructions (Ni-NTA; Qiagen). Polyclonal antibodies were prepared by injection of the purified fusion protein into two female New Zealand White rabbits (HRP Inc., Pennsylvania). Purified 6His-tagged hsMad2 was coupled to CNBr-activated Sepharose 4B (Pharmacia) according to the manufacturer's instructions to generate the hsMad2 affinity column. The α-hsMad2 polyclonal serum was loaded onto the affinity column and the α-hsMad2 antibody was eluted from the column with 0.1M glycine [pH 2.5] (22). A negative control antibody (α-hsMad2D IgG) was prepared by passing the flowthrough of the affinity column over a Protein A-Sepharose column (Pharmacia) and eluting the IgG fraction with 0.1M glycine [pH 2.5] (22). IgG from the corresponding preimmune serum was also isolated using a Protein A-Sepharose column (Pharmacia). All of the purified IgGs were extensively dialyzed against PBS and concentrated to 2 mg/ml (α-hsMad2 IgG and α-hsMad2Δ IgG) or 1.5 mg/ml (preimmune IgG) using the Centricon-30 units (Amicon) according to the manufacturer's instructions.
22. Harlow, E. & Lane, D. *Antibodies: A Laboratory Manual* (Cold Spring Harbor Laboratory, Cold Spring Harbor, N.Y., 1988).
23. Protein extracts were prepared by lysing cells in NP-40 lysis buffer (50 mM Tris [pH 7.5], 150 mM NaCl, 1% NP-40, 10% glycerol, 2 mM EDTA, 50 mM NaF, 0.25 mM $Na_3VO_4$, 1 mM PMSF, and 5 µg/ml of aprotinin, antipain, pepstatin, and leupeptin). Protein extracts were resolved by 12% SDS-PAGE and transferred to nitrocellulose membranes (Bio-Rad) as described (22). Immunoblotting was performed using the enhanced chemiluminescence protocol (DuPont NEN) according to the manufacturer's instructions. The affinity purified antibodies were used at 0.8 µg/ml and the donkey anti-rabbit IgG HRP (horseradish peroxidase)—linked secondary antibody (Amersham) was used at 1:10,000.
24. HeLa cells were split into fresh medium one day before electroporation. Cells were harvested, washed, and resuspended in PBS to $1 \times 10^7$ cells/ml. $1 \times 10^6$ cells were mixed with approximately 25 µg of affinity-purified antibodies and incubated for 10 min at room temperature in 0.4 cm Gene Pulser cuvettes. The electric pulse was delivered from a Gene Pulser (Bio-Rad) set at 300 V, infinite resistance, 250 µF. Immediately after the pulse, cells were transferred into 6-well dishes containing pre-warmed medium and allowed to firmly attach to the dishes for 6 hr. Cells were then exposed to either 100 nM or 200 nM nocodazole for 12 or 18 hr before being photographed. Cells were trypsinized off the dishes and transferred to slides by cytospinning at 500 rpm for 6 min. Cells were fixed and stained with DAPI and anti-rabbit IgG secondary antibody (27). IgG⁺cells and IgG mitotic cells were counted by immunofluorescence microscopy (27).

25. Goh, P., and Kilmartin, J. V. *J. Cell Biol.* 121, 503–512 (1993).
26. Wang, Y., and Burke, D. J. Mol. *Cell. Biol.* 15, 6838–6844 (1995).
27. Cells were fixed at −20° C. with 100% methanol for 6 min and permeabilized at −20° C. with 100% acetone for 30 s. Cells were then washed with PBS and blocked with 3% BSA in PBS for 1 hr. For staining of hsMad2, affinity purified antibody was used at 2 µg/ml in the blocking buffer for 1 hr at room temperature. Cells were then washed six times with PBS containing 0.1% Triton X-100 and incubated for 30 min with 1:50 diluted donkey anti-rabbit IgG FITC-conjugated secondary antibody (Amersham). After six washes in PBS, cells were stained with DAPI (0.1 µg/ml in PBS), washed again, and mounted. For co-immunostaining of hsMad2 and centromeres, cells were incubated with both affinity-purified α-hsMad2 antibody (2 µg/ml) and human α-centromere serum (1:100 diluted) derived from a scleroderma patient (a gift from Dr. Keith Elkon at Cornell University Medical Center) for 1 hr, washed as described above, and then incubated with donkey anti-rabbit IgG FITC-conjugated secondary antibody (1:50, Jackson ImmunoResearch) and donkey anti-human IgG Rhodamine-labeled secondary antibody (1:50, Jackson ImmunoResearch). All cells were analyzed with a Zeiss Axiophot microscope.
28. Jordan, M. A., Thrower, D., and Wilson, L. J. *Cell Sci.* 102, 401–416 (1992).
29. Graham, M. L., et al. Cancer Res. 50, 6208–6217 (1990).
30. Dellarco, V., Voytek, P. & Hollander, A. Aneuploidy: Etiology and Mechanisms (Plenum, N.Y., 1985).

---

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
　　　　(A) LENGTH: 205 amino acids
　　　　(B) TYPE: amino acid
　　　　(C) STRANDEDNESS: single
　　　　(D) TOPOLOGY: linear (ii) MOLECULE TYPE: protein (xi) SEQUENCE DESCRIPTION: SEQ ID NO:1:

```
Met Ala Leu Gln Leu Ser Arg Glu Gln Gly Ile Thr Leu Arg Gly Ser
 1               5                  10                  15

Ala Glu Ile Val Ala Glu Phe Phe Ser Phe Gly Ile Asn Ser Ile Leu
                20                  25                  30

Tyr Gln Arg Gly Ile Tyr Pro Ser Glu Thr Phe Thr Arg Val Gln Lys
            35                  40                  45

Tyr Gly Leu Thr Leu Leu Val Thr Thr Asp Leu Glu Leu Ile Lys Tyr
        50                  55                  60

Leu Asn Asn Val Val Glu Gln Leu Lys Asp Trp Leu Tyr Lys Cys Ser
 65                  70                  75                  80

Val Gln Lys Leu Val Val Val Ile Ser Asn Ile Glu Ser Gly Glu Val
                85                  90                  95

Leu Glu Arg Trp Gln Phe Asp Ile Glu Cys Asp Lys Thr Ala Lys Asp
                100                 105                 110

Asp Ser Ala Pro Arg Glu Lys Ser Gln Lys Ala Ile Gln Asp Glu Ile
            115                 120                 125

Arg Ser Val Ile Arg Gln Ile Thr Ala Thr Val Thr Phe Leu Pro Leu
        130                 135                 140

Leu Glu Val Ser Cys Ser Phe Asp Leu Leu Ile Tyr Thr Asp Lys Asp
145                 150                 155                 160

Leu Val Val Pro Glu Lys Trp Glu Glu Ser Gly Pro Gln Phe Ile Thr
                165                 170                 175

Asn Ser Glu Glu Val Arg Leu Arg Ser Phe Thr Thr Thr Ile His Lys
```

|     |     |     |     |     | 180 |     |     |     |     | 185 |     |     |     |     | 190 |
| --- | --- | --- | --- | --- | --- | --- | --- | --- | --- | --- | --- | --- | --- | --- | --- |
| Val | Asn | Ser | Met | Val | Ala | Tyr | Lys | Ile | Pro | Val | Asn | Asp |
|     |     | 195 |     |     |     |     | 200 |     |     |     |     | 205 |

(2) INFORMATION FOR SEQ ID NO:2:

(i) SEQUENCE CHARACTERISTICS:
        (A) LENGTH: 196 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

| Met | Ser | Gln | Ser | Ile | Ser | Leu | Lys | Gly | Ser | Thr | Arg | Thr | Val | Thr | Glu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Phe | Phe | Glu | Tyr | Ser | Ile | Asn | Ser | Ile | Leu | Tyr | Gln | Arg | Gly | Val | Tyr |
|     |     |     | 20  |     |     |     | 25  |     |     |     |     | 30  |     |     |     |
| Pro | Ala | Glu | Asp | Phe | Val | Thr | Val | Lys | Lys | Tyr | Asp | Leu | Thr | Leu | Leu |
|     |     | 35  |     |     |     |     | 40  |     |     |     |     | 45  |     |     |     |
| Lys | Thr | His | Asp | Asp | Glu | Leu | Lys | Asp | Tyr | Ile | Arg | Lys | Ile | Leu | Leu |
|     | 50  |     |     |     |     | 55  |     |     |     |     | 60  |     |     |     |     |
| Gln | Val | His | Arg | Trp | Leu | Leu | Gly | Gly | Lys | Cys | Asn | Gln | Leu | Val | Leu |
| 65  |     |     |     | 70  |     |     |     |     | 75  |     |     |     |     | 80  |     |
| Cys | Ile | Val | Asp | Lys | Asp | Glu | Gly | Glu | Val | Val | Glu | Arg | Trp | Ser | Phe |
|     |     |     |     | 85  |     |     |     |     | 90  |     |     |     |     | 95  |     |
| Asn | Val | Gln | His | Ile | Ser | Gly | Asn | Ser | Asn | Gly | Gln | Asp | Asp | Val | Val |
|     |     |     | 100 |     |     |     |     | 105 |     |     |     |     | 110 |     |     |
| Asp | Leu | Asn | Thr | Thr | Gln | Ser | Gln | Ile | Arg | Ala | Leu | Ile | Arg | Gln | Ile |
|     |     | 115 |     |     |     |     | 120 |     |     |     |     | 125 |     |     |     |
| Thr | Ser | Ser | Val | Thr | Phe | Leu | Pro | Glu | Leu | Thr | Lys | Glu | Gly | Gly | Tyr |
|     | 130 |     |     |     |     | 135 |     |     |     |     | 140 |     |     |     |     |
| Thr | Phe | Thr | Val | Leu | Ala | Tyr | Thr | Asp | Ala | Asp | Ala | Lys | Val | Pro | Leu |
| 145 |     |     |     |     | 150 |     |     |     |     | 155 |     |     |     |     | 160 |
| Glu | Trp | Ala | Asp | Ser | Asn | Ser | Lys | Glu | Ile | Pro | Asp | Gly | Glu | Val | Val |
|     |     |     |     | 165 |     |     |     |     | 170 |     |     |     |     | 175 |     |
| Gln | Phe | Lys | Thr | Phe | Ser | Thr | Asn | Asp | His | Lys | Val | Gly | Ala | Gln | Val |
|     |     |     | 180 |     |     |     |     | 185 |     |     |     |     | 190 |     |     |
| Ser | Tyr | Lys | Tyr |
|     |     | 195 |     |

(2) INFORMATION FOR SEQ ID NO:3:

(i) SEQUENCE CHARACTERISTICS:
        (A) LENGTH: 618 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
ATGGCGCTGC AGCTCTCCCG GGAGCAGGGA ATCACCCTGC GCGGGAGCGC CGAAATCGTG        60
GCCGAGTTCT TCTCATTCGG CATCAACAGC ATTTTATATC AGCGTGGCAT ATATCCATCT       120
GAAACCTTTA CTCGAGTGCA GAAATACGGA CTCACCTTGC TTGTAACTAC TGATCTTGAG       180
CTCATAAAAT ACCTAAATAA TGTGGTGGAA CAACTGAAAG ATTGGTTATA CAAGTGTTCA       240
GTTCAGAAAC TGGTTGTAGT TATCTCAAAT ATTGAAAGTG GTGAGGTCCT GGAAAGATGG       300
```

| | | | | | |
|---|---|---|---|---|---|
| CAGTTTGATA | TTGAGTGTGA | CAAGACTGCA | AAAGATGACA | GTGCACCCAG | AGAAAAGTCT | 360 |
| CAGAAAGCTA | TCCAGGATGA | AATCCGTTCA | GTGATCAGAC | AGATCACAGC | TACGGTGACA | 420 |
| TTTCTGCCAC | TGTTGGAAGT | TTCTTGTTCA | TTTGATCTGC | TGATTTATAC | AGACAAAGAT | 480 |
| TTGGTTGTAC | CTGAAAAATG | GGAAGAGTCG | GGACCACAGT | TTATTACCAA | TTCTGAGGAA | 540 |
| GTGCGCCTTC | GTTCATTTAC | TACTACAATC | CACAAAGTAA | ATAGCATGGT | GGCCTACAAA | 600 |
| ATTCCTGTCA | ATGACTGA | | | | | 618 |

( 2 ) INFORMATION FOR SEQ ID NO:4:

( i ) SEQUENCE CHARACTERISTICS:
        ( A ) LENGTH: 591 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| ATGTCACAAT | CAATATCACT | AAAGGGTTCA | ACAAGGACAG | TTACAGAATT | TTTCGAGTAC | 60 |
| AGCATTAATT | CCATTTTGTA | CCAAAGAGGC | GTATACCCAG | CAGAAGATTT | CGTAACGGTG | 120 |
| AAAAAGTACG | ATCTTACGTT | ACTAAAGACA | CATGATGATG | AACTGAAAG | ATTACATTCGG | 180 |
| AAAATTCTT | CTACAAGTTC | ACAGGTGGCT | TCTTGGTGGA | AAATGCAATC | AATTAGTATTA | 240 |
| TGTATTGTA | GACAAGGATG | AGGGAGAGGT | GGTGGAAAGA | TGGTCCTTCA | ATGTGCAACAC | 300 |
| ATTTCTGGC | AATAGCAACG | GGCAGGATGA | TGTTGTAGAT | TTAAATACAA | CACAATCACAA | 360 |
| ATCAGAGCT | TTAATCAGGC | AAATCACCTC | AAGCGTTACC | TTTCTGCCCG | AACTAACAAA | 420 |
| GAAGGTGGG | TACACATTCA | CAGTACTTGC | ATATACAGAC | GCGGATGCTA | AAGTTCCGTTA | 480 |
| GAATGGGCC | GACTCCAATA | GTAAAGAGAT | ACCTGATGGT | GAAGTAG | TTCAATTCAAAACA | 540 |
| TTCTCT | ACCAACGATC | ATAAAGTTGG | TGCGCAGGTC | AGCTATAAAT | ATTAA | 591 |

( 2 ) INFORMATION FOR SEQ ID NO:5:

( i ) SEQUENCE CHARACTERISTICS:
        ( A ) LENGTH: 1484 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 34..648

( x i ) SEQUENCE DESCRIPTION: SEQ ID NO:5:

```
TGGAAGCGCG  TGCTTTTGTT  TGTGTCCCTG  GCC ATG GCG CTG CAG CTC TCC CGG          54
                                        Met Ala Leu Gln Leu Ser Arg
                                         1               5

GAG CAG GGA ATC ACC CTG CGC GGG AGC GCC GAA ATC GTG GCC GAG TTC             102
Glu Gln Gly Ile Thr Leu Arg Gly Ser Ala Glu Ile Val Ala Glu Phe
            10                  15                  20

TTC TCA TTC GGC ATC AAC AGC ATT TTA TAT CAG CGT GGC ATA TAT CCA             150
Phe Ser Phe Gly Ile Asn Ser Ile Leu Tyr Gln Arg Gly Ile Tyr Pro
        25                  30                  35

TCT GAA ACC TTT ACT CGA GTG CAG AAA TAC GGA CTC ACC TTG CTT GTA             198
Ser Glu Thr Phe Thr Arg Val Gln Lys Tyr Gly Leu Thr Leu Leu Val
 40                  45                  50                  55

ACT ACT GAT CTT GAG CTC ATA AAA TAC CTA AAT AAT GTG GTG GAA CAA             246
Thr Thr Asp Leu Glu Leu Ile Lys Tyr Leu Asn Asn Val Val Glu Gln
```

| | | | | | | | | | | | | | | | | |
|---|---|---|---|---|---|---|---|---|---|---|---|---|---|---|---|---|
| | | | | 60 | | | | | 65 | | | | | 70 | | |
| CTG | AAA | GAT | TGG | TTA | TAC | AAG | TGT | TCA | GTT | CAG | AAA | CTG | GTT | GTA | GTT | 294 |
| Leu | Lys | Asp | Trp | Leu | Tyr | Lys | Cys | Ser | Val | Gln | Lys | Leu | Val | Val | Val | |
| | | | 75 | | | | 80 | | | | | 85 | | | | |
| ATC | TCA | AAT | ATT | GAA | AGT | GGT | GAG | GTC | CTG | GAA | AGA | TGG | CAG | TTT | GAT | 342 |
| Ile | Ser | Asn | Ile | Glu | Ser | Gly | Glu | Val | Leu | Glu | Arg | Trp | Gln | Phe | Asp | |
| | | 90 | | | | | 95 | | | | 100 | | | | | |
| ATT | GAG | TGT | GAC | AAG | ACT | GCA | AAA | GAT | GAC | AGT | GCA | CCC | AGA | GAA | AAG | 390 |
| Ile | Glu | Cys | Asp | Lys | Thr | Ala | Lys | Asp | Asp | Ser | Ala | Pro | Arg | Glu | Lys | |
| | 105 | | | | 110 | | | | | 115 | | | | | | |
| TCT | CAG | AAA | GCT | ATC | CAG | GAT | GAA | ATC | CGT | TCA | GTG | ATC | AGA | CAG | ATC | 438 |
| Ser | Gln | Lys | Ala | Ile | Gln | Asp | Glu | Ile | Arg | Ser | Val | Ile | Arg | Gln | Ile | |
| 120 | | | | 125 | | | | | 130 | | | | | 135 | | |
| ACA | GCT | ACG | GTG | ACA | TTT | CTG | CCA | CTG | TTG | GAA | GTT | TCT | TGT | TCA | TTT | 486 |
| Thr | Ala | Thr | Val | Thr | Phe | Leu | Pro | Leu | Leu | Glu | Val | Ser | Cys | Ser | Phe | |
| | | | | 140 | | | | 145 | | | | | 150 | | | |
| GAT | CTG | CTG | ATT | TAT | ACA | GAC | AAA | GAT | TTG | GTT | GTA | CCT | GAA | AAA | TGG | 534 |
| Asp | Leu | Leu | Ile | Tyr | Thr | Asp | Lys | Asp | Leu | Val | Val | Pro | Glu | Lys | Trp | |
| | | | 155 | | | | | 160 | | | | | 165 | | | |
| GAA | GAG | TCG | GGA | CCA | CAG | TTT | ATT | ACC | AAT | TCT | GAG | GAA | GTG | CGC | CTT | 582 |
| Glu | Glu | Ser | Gly | Pro | Gln | Phe | Ile | Thr | Asn | Ser | Glu | Glu | Val | Arg | Leu | |
| | | 170 | | | | | 175 | | | | | 180 | | | | |
| CGT | TCA | TTT | ACT | ACT | ACA | ATC | CAC | AAA | GTA | AAT | AGC | ATG | GTG | GCC | TAC | 630 |
| Arg | Ser | Phe | Thr | Thr | Thr | Ile | His | Lys | Val | Asn | Ser | Met | Val | Ala | Tyr | |
| | 185 | | | | | 190 | | | | | 195 | | | | | |
| AAA | ATT | CCT | GTC | AAT | GAC | TGAGGATGAC | | ATGAGGAAAA | | TAATGTAAT | | | | | | 677 |
| Lys | Ile | Pro | Val | Asn | Asp | | | | | | | | | | | |
| 200 | | | | | 205 | | | | | | | | | | | |

| | | |
|---|---|---|
| TGTAATTTTG AAATGTGGTT TTCCTGAAAT CAGGTCATCT ATAGTTGATA TGTTTTATTT | | 737 |
| CATTGGTTAA TTTTTACATG GAGAAAACCA AAATGATACT TACTGAACTG TGTGTAATTG | | 797 |
| TTCCTTTTAT TTTTTTGGTA CCTATTTGAC TTACCATGGA GTTAACATCA TGAATTTATT | | 857 |
| GCACATTGTT CAAAAGGAAC CAGGAGGTTT TTTTGTCAAC ATTGTGATGT ATATTCCTTT | | 917 |
| GAAGATAGTA ACTGTAGATG GAAAAACTTG TGCTATAAAG CTAGATGCTT TCCTAAATCA | | 977 |
| GATGTTTTGG TCAAGTAGTT TGACTCAGTA TAGGTAGGGA GATATTTAAG TATAAAATAC | | 1037 |
| AACAAAGGAA GTCTAAATAT TCAGAATCTT TGTTAAGGTC CTGAAAGTAA CTCATAATCT | | 1097 |
| ATAAACAATG AAATATTGCT GTATAGCTCC TTTTGACCTT CATTTCATGT ATAGTTTTCC | | 1157 |
| CTATTGAATC AGTTCCAAT TATTTGACTT TAATTTATGT AACTTGAACC TATGAAGCAA | | 1217 |
| TGGATATTTG TACTGTTTAA TGTTCTGTGA TACAGAACAG ATTAATACTC CCTTTTTATC | | 1277 |
| ATTACAGTTA GCTAAAAAAT TGCCAGGCAG TCCACAAAAC AGAATTTGCT TTAAGACCAA | | 1337 |
| CCCACAGAGT CAGCTGGAGA CTAACGGCGC TGGGGCCTGC TGGGCCGGGA TATAGTCGTG | | 1397 |
| TTTAGCTAAG TGTCGAGAGC ATTAAGAAGA AAGTCCTGGT TGGAGGCGCA AGGCCTGCAG | | 1457 |
| CACCAGCTGT GGAATCCCCA ATAATGT | | 1484 |

( 2 ) INFORMATION FOR SEQ ID NO:6:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Ala | Leu | Gln | Leu | Ser | Arg | Glu | Gln | Gly | Ile | Thr | Leu | Arg | Gly | Ser |
| 1 | | | | 5 | | | | | 10 | | | | | 15 | |

|     |     |     |     |     |     |     |     |     |     |     |     |     |     |     |
|-----|-----|-----|-----|-----|-----|-----|-----|-----|-----|-----|-----|-----|-----|-----|
| Ala | Glu | Ile | Val<br>20 | Ala | Glu | Phe | Phe | Ser<br>25 | Phe | Gly | Ile | Asn | Ser<br>30 | Ile | Leu |
| Tyr | Gln | Arg<br>35 | Gly | Ile | Tyr | Pro | Ser<br>40 | Glu | Thr | Phe | Thr | Arg<br>45 | Val | Gln | Lys |
| Tyr | Gly<br>50 | Leu | Thr | Leu | Leu | Val<br>55 | Thr | Thr | Asp | Leu | Glu<br>60 | Leu | Ile | Lys | Tyr |
| Leu<br>65 | Asn | Asn | Val | Val | Gln<br>70 | Leu | Lys | Asp | Trp | Leu<br>75 | Tyr | Lys | Cys | Ser<br>80 |
| Val | Gln | Lys | Leu | Val<br>85 | Val | Val | Ile | Ser | Asn<br>90 | Ile | Glu | Ser | Gly | Glu<br>95 | Val |
| Leu | Glu | Arg | Trp<br>100 | Gln | Phe | Asp | Ile | Glu<br>105 | Cys | Asp | Lys | Thr | Ala<br>110 | Lys | Asp |
| Asp | Ser | Ala<br>115 | Pro | Arg | Glu | Lys | Ser<br>120 | Gln | Lys | Ala | Ile | Gln<br>125 | Asp | Glu | Ile |
| Arg | Ser<br>130 | Val | Ile | Arg | Gln | Ile<br>135 | Thr | Ala | Thr | Val | Thr<br>140 | Phe | Leu | Pro | Leu |
| Leu<br>145 | Glu | Val | Ser | Cys | Ser<br>150 | Phe | Asp | Leu | Leu | Ile<br>155 | Tyr | Thr | Asp | Lys | His<br>160 |
| Leu | Val | Val | Pro | Glu<br>165 | Lys | Trp | Glu | Glu | Ser<br>170 | Gly | Pro | Gln | Phe | Ile<br>175 | Thr |
| Asn | Ser | Glu | Glu<br>180 | Val | Arg | Leu | Arg | Ser<br>185 | Phe | Thr | Thr | Thr | Ile<br>190 | His | Lys |
| Val | Asn | Ser<br>195 | Met | Val | Ala | Tyr | Lys<br>200 | Ile | Pro | Val | Asn | Asp<br>205 |

( 2 ) INFORMATION FOR SEQ ID NO:7:

( i ) SEQUENCE CHARACTERISTICS:
        ( A ) LENGTH: 205 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

|     |     |     |     |     |     |     |     |     |     |     |     |     |     |     |     |
|-----|-----|-----|-----|-----|-----|-----|-----|-----|-----|-----|-----|-----|-----|-----|-----|
| Met<br>1 | Ala | Leu | Gln | Leu<br>5 | Ser | Arg | Glu | Gln | Gly<br>10 | Ile | Thr | Leu | Arg | Gly<br>15 | Ser |
| Ala | Glu | Ile | Val<br>20 | Ala | Glu | Phe | Phe | Ser<br>25 | Phe | Gly | Ile | Asn | Ser<br>30 | Ile | Leu |
| Tyr | Gln | Arg<br>35 | Gly | Ile | Tyr | Pro | Ser<br>40 | Glu | Thr | Phe | Thr | Arg<br>45 | Val | Gln | Lys |
| Tyr | Gly<br>50 | Leu | Thr | Leu | Leu | Val<br>55 | Thr | Thr | Asp | Leu | Glu<br>60 | Leu | Ile | Lys | Tyr |
| Leu<br>65 | Asn | Asn | Val | Val | Gln<br>70 | Leu | Lys | Asp | Trp | Leu<br>75 | Tyr | Lys | Cys | Ser<br>80 |
| Val | Gln | Lys | Leu | Val<br>85 | Val | Val | Ile | Ser | Asn<br>90 | Ile | Glu | Ser | Gly | Glu<br>95 | Val |
| Leu | Glu | Arg | Trp<br>100 | Gln | Phe | Asp | Ile | Glu<br>105 | Cys | Asp | Lys | Thr | Ala<br>110 | Lys | Asp |
| Asp | Ser | Ala<br>115 | Pro | Arg | Glu | Lys | Ser<br>120 | Gln | Lys | Ala | Ile | Gln<br>125 | Asp | Glu | Ile |
| Arg | Ser<br>130 | Val | Ile | Arg | Gln | Ile<br>135 | Thr | Ala | Thr | Val | Thr<br>140 | Phe | Leu | Pro | Leu |
| Leu<br>145 | Glu | Val | Ser | Cys | Ser<br>150 | Phe | Asp | Leu | Leu | Ile<br>155 | Tyr | Thr | Asp | Lys | Asp<br>160 |

```
Leu  Val  Val  Pro  Glu  Lys  Trp  Glu  Glu  Ser  Gly  Pro  Gln  Phe  Ile  Thr
               165                      170                      175

Asn  Ser  Glu  Glu  Val  Arg  Leu  Arg  Ser  Phe  Thr  Thr  Thr  Ile  His  Lys
               180                      185                      190

Val  Asn  Ser  Met  Val  Ala  Tyr  Lys  Ile  Pro  Val  Asn  Asp
               195                      200                 205
```

( 2 ) INFORMATION FOR SEQ ID NO:8:

( i ) SEQUENCE CHARACTERISTICS:
        ( A ) LENGTH: 203 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Met  Ala  Gly  Gln  Leu  Thr  Arg  Glu  Gly  Ile  Thr  Leu  Lys  Gly  Ser  Ala
1                   5                        10                      15

Glu  Ile  Val  Ser  Glu  Phe  Phe  Cys  Gly  Ile  Asn  Ser  Ile  Leu  Tyr
               20                  25                      30

Gln  Arg  Gly  Ile  Tyr  Pro  Ser  Glu  Thr  Phe  Thr  Ile  Arg  Gln  Lys  Tyr
               35                       40                      45

Gly  Leu  Thr  Leu  Leu  Val  Ser  Thr  Asp  Pro  Ala  Leu  Lys  Glu  Tyr  Leu
     50                       55                           60

Asn  Lys  Val  Thr  Asp  Gln  Leu  Lys  Asp  Trp  Leu  Tyr  Lys  Cys  Gln  Val
65                  70                       75                           80

Gln  Lys  Leu  Val  Val  Val  Ile  Thr  Ser  Ile  Asp  Ser  Asn  Glu  Ile  Leu
               85                       90                           95

Glu  Arg  Trp  Gln  Phe  Asp  Ile  Glu  Cys  Asp  Lys  Thr  Val  Lys  Asp  Gly
               100                      105                     110

Ile  Val  Arg  Glu  Lys  Ser  Gln  Lys  Val  Ile  Gln  Glu  Ile  Arg  Ser
               115                      120                     125

Val  Ile  Arg  Gln  Ile  Thr  Ala  Thr  Val  Thr  Phe  Leu  Pro  Leu  Leu  Glu
               130                      135                     140

Thr  Ala  Cys  Ala  Phe  Asp  Leu  Leu  Ile  Tyr  Thr  Asp  Lys  Asp  Leu  Glu
145                      150                      155                      160

Val  Pro  Glu  Lys  Trp  Glu  Glu  Ser  Gly  Pro  Gln  Phe  Val  Ser  Asn  Ser
               165                      170                      175

Glu  Glu  Val  Arg  Leu  Arg  Ser  Phe  Thr  Thr  Thr  Ile  His  Lys  Val  Asn
               180                      185                      190

Ser  Met  Val  Ala  Tyr  Lys  Lys  Ile  Asp  Thr  Phe
               195                      200
```

( 2 ) INFORMATION FOR SEQ ID NO:9:

( i ) SEQUENCE CHARACTERISTICS:
        ( A ) LENGTH: 196 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Met  Ser  Gln  Ser  Ile  Ser  Leu  Lys  Gly  Ser  Thr  Arg  Thr  Val  Thr  Glu
1                   5                        10                      15

Phe  Phe  Glu  Tyr  Ser  Ile  Asn  Ser  Ile  Leu  Tyr  Gln  Arg  Gly  Val  Tyr
               20                       25                      30
```

-continued

| | | | | | | | | | | | | | | |
|---|---|---|---|---|---|---|---|---|---|---|---|---|---|---|
| Pro | Ala | Glu<br>35 | Asp | Phe | Val | Thr | Val<br>40 | Lys | Lys | Tyr | Asp | Leu<br>45 | Thr | Leu | Leu |
| Lys | Thr<br>50 | His | Asp | Asp | Glu | Leu<br>55 | Lys | Asp | Tyr | Ile | Arg<br>60 | Lys | Ile | Leu | Leu |
| Gln<br>65 | Val | His | Arg | Trp | Leu<br>70 | Leu | Gly | Gly | Lys | Cys<br>75 | Asn | Gln | Leu | Val | Leu<br>80 |
| Cys | Ile | Val | Asp | Lys<br>85 | Asp | Glu | Gly | Glu | Val<br>90 | Val | Glu | Arg | Trp | Ser<br>95 | Phe |
| Asn | Val | Gln | His<br>100 | Ile | Ser | Gly | Asn | Ser<br>105 | Asn | Gly | Gln | Asp | Asp<br>110 | Val | Val |
| Asp | Leu | Asn<br>115 | Thr | Thr | Gln | Ser | Gln<br>120 | Ile | Arg | Ala | Leu | Ile<br>125 | Arg | Gln | Ile |
| Thr | Ser<br>130 | Ser | Val | Thr | Phe | Leu<br>135 | Pro | Glu | Leu | Thr | Lys<br>140 | Glu | Gly | Gly | Tyr |
| Thr<br>145 | Phe | Thr | Val | Leu | Ala<br>150 | Tyr | Thr | Asp | Ala | Asp<br>155 | Ala | Lys | Val | Pro | Leu<br>160 |
| Glu | Trp | Ala | Asp | Ser<br>165 | Asn | Ser | Lys | Glu | Ile<br>170 | Pro | Asp | Gly | Glu | Val<br>175 | Val |
| Gln | Phe | Lys | Thr<br>180 | Phe | Ser | Thr | Asn | Asp<br>185 | His | Lys | Val | Gly | Ala<br>190 | Gln | Val |
| Ser | Tyr | Lys<br>195 | Tyr | | | | | | | | | | | | |

What is claimed is:

1. An isolated nucleic acid encoding human MAD2 protein wherein the nucleic acid encodes a protein comprising the amino acid sequence of SEQ ID NO: 6.

2. The isolated nucleic acid of claim 1, wherein the nucleic acid is DNA.

3. The isolated nucleic acid of claim 2, wherein the DNA is genomic DNA.

4. The isolated nucleic acid of claim 2, wherein the DNA is cDNA.

5. The isolated nucleic acid of claim 4, wherein the nucleic acid comprises the nucleic acid sequence of SEQ ID NO: 5.

6. The isolated nucleic acid of claim 1, wherein the nucleic acid is RNA.

7. The isolated nucleic acid of claim 6, wherein the nucleic acid is mRNA.

8. A vector comprising the nucleic acid of claim 1.

9. A host cell containing the vector of claim 8.

10. The host cell of claim 9, wherein the cell is a prokaryotic or eukaryotic cell.

11. The host cell of claim 9, wherein the prokaryotic cell is a bacterial cell.

12. The host cell of claim 9, wherein the eukaryotic cell is a yeast, insect, plant, or mammalian cell.

* * * * *